United States Patent
McGall et al.

(10) Patent No.: US 6,238,862 B1
(45) Date of Patent: May 29, 2001

(54) METHODS FOR TESTING OLIGONUCLEOTIDE ARRAYS

(75) Inventors: Glenn McGall, Mountain View; Anthony D. Barone, Santa Clara, both of CA (US); Martin Diggelmann, Arlesheim (CH); David J. Lockhart, Santa Clara, CA (US); Ann Maria Caviani Pease, Sunnyvale, CA (US); Mark Chee, Palo Alto, CA (US)

(73) Assignee: Affymetrix, Inc., Santa Clara, CA (US)

( * ) Notice: Subject to any disclaimer, the term of this patent is extended or adjusted under 35 U.S.C. 154(b) by 0 days.

(21) Appl. No.: 08/995,265

(22) Filed: Dec. 19, 1997

Related U.S. Application Data

(63) Continuation of application No. 08/531,155, filed on Sep. 18, 1995, now Pat. No. 5,843,655.

(51) Int. Cl.[7] ............................................. C12Q 1/68
(52) U.S. Cl. .................... 435/6; 536/22.1; 536/23.1; 536/25.3; 536/25.32
(58) Field of Search ........................... 435/6; 536/22.1, 536/23.1, 25.3, 25.32; 436/518, 528, 527

(56) References Cited

U.S. PATENT DOCUMENTS

| | | | |
|---|---|---|---|
| 4,775,619 | * 10/1988 | Urdea | 435/6 |
| 5,008,617 | * 4/1991 | Czubatyj et al. | 324/158 R |
| 5,143,854 | 9/1992 | Pirrung et al. | 436/518 |
| 5,324,633 | 6/1994 | Fodor et al. | 435/6 |

FOREIGN PATENT DOCUMENTS

| | | | |
|---|---|---|---|
| 90/15070 | 6/1990 | (WO) | C07K/1/04 |
| 92/10092 | 11/1991 | (WO) | A01N/1/02 |
| 95/00530 | 1/1995 | (WO) | C07H/21/04 |

OTHER PUBLICATIONS

Pease, Ann Caviani, et al., "Light–generated oligonucleotide arrays for rapid DNA sequence analysis," Proc. Natl. Acad. Sci. USA, vol. 91, pp. 5022–5026, May 1994.

* cited by examiner

Primary Examiner—Jezia Riley
(74) Attorney, Agent, or Firm—Townsend and Townsend and Crew LLP

(57) ABSTRACT

Methods for testing oligonucleotide arrays are disclosed including methods for testing the efficiency of nucleotide coupling; methods for testing amounts of deprotected oligonucleotides; methods for determining amounts of depurinated oligonucleotides; and methods of detecting the presence of cleavable structural features, such as double-stranded nucleic acids.

39 Claims, 15 Drawing Sheets

METHODS FOR TESTING OLIGONUCLEOTIDE ARRAYS

This application is a continuation of and claims the benefit of U.S. application Ser. No. 08/531,155, filed Sep. 18, 1995, now U.S. Pat. No. 5,843,655 the disclosure of which is incorporated by reference.

BACKGROUND OF THE INVENTION

This invention relates to methods for testing the effect of various conditions on oligonucleotide arrays before, during of after production. The invention therefore relates to the fields of quality control in manufacturing and chemical assays.

New technology, called VLSIPS™, has enabled the production of chips smaller than a thumbnail that contain hundreds of thousands or more of different molecular probes. These techniques are described in U.S. Pat. No. 5,143,854, PCT WO 92/10092, and PCT WO 90/15070. Biological chips have probes arranged in arrays, each probe ensemble assigned a specific location. Biological chips have been produced in which each location has a scale of, for example, ten microns. The chips can be used to determine whether target molecules interact with any of the probes on the chip. After exposing the array to target molecules under selected test conditions, scanning devices can examine each location in the array and determine whether a target molecule has interacted with the probe at that location.

Biological chips are useful in a variety of screening techniques for obtaining information about either the probes or the target molecules. For example, a library of peptides can be used as probes to screen for drugs. The peptides can be exposed to a receptor, and those probes that bind to the receptor can be identified.

Biological chips wherein the probes are oligonucleotides ("oligonucleotide arrays") show particular promise. Arrays of nucleic acid probes can be used to extract sequence information from nucleic acid samples. The samples are exposed to the probes under conditions that allow hybridization. The arrays are then scanned to determine to which probes the sample molecules have hybridized. One can obtain sequence information by selective tiling of the probes with particular sequences on the arrays, and using algorithms to compare patterns of hybridization and non-hybridization. This method is useful for sequencing nucleic acids. It is also useful in diagnostic screening for genetic diseases or for the presence of a particular pathogen or a strain of pathogen.

The scaled-up manufacturing of oligonucleotide arrays requires application of quality control standards both for determining the quality of chips under current manufacturing conditions and for identifying optimal conditions for their manufacture. Quality control, of course, is not limited to manufacture of chips, but also to the conditions under which they are stored, transported and, ultimately, used.

SUMMARY OF THE INVENTION

This invention provides methods for testing the quality of biological chips and the effect of various parameters used in their production by manufacturing oligonucleotide arrays by spatially directed oligonucleotide synthesis in high volume and testing selected arrays. In one embodiment the methods involve determining the extent to which a test condition causes the appearance of a structural feature in oligonucleotides produced on an oligonucleotide array by spatially directed oligonucleotide synthesis by providing a substrate having a surface with linkers having an active site for oligonucleotide synthesis; synthesizing an ensemble of sequence-specific oligonucleotides on the substrate by spatially directed oligonucleotide synthesis, the oligonucleotides optionally having active sites for attaching a detectable label; exposing the area to the test condition; and determining the amount of oligonucleotides having the structural feature.

Certain of the methods of this invention test the efficiency of nucleotide coupling in the synthesis of an oligonucleotide array by spatially directed oligonucleotide synthesis. One of these methods to test efficiency involves providing a substrate having a surface having linkers with active sites; coupling first protected nucleotides to active sites in a first area and second areas of the substrate and capping unreacted, unprotected active sites; deprotecting active sites in the second areas, coupling protected nucleotides to active sites in the second areas and capping unreacted, unprotected active sites in the second areas; optionally repeating the previous step in at least one subsequent area of the substrate and capping unreacted, unprotected active sites in the subsequent areas; determining the amount of competent, uncapped active sites in at least two areas; and comparing the amounts determined. The comparative amount indicates the efficiency of nucleotide coupling between the two areas.

Another method of testing the efficiency of nucleotide coupling involves the steps of providing a substrate having a surface having cleavable linkers including a detectable label and active sites for nucleotide coupling; coupling at least one nucleotide to the active sites and capping unreacted, unprotected active sites after at least one coupling step; cleaving the cleavable linker to release detectably labelled oligonucleotides; determining the lengths of the released oligonucleotides; and comparing the amounts of oligonucleotides having a first length and a second length. The comparative amount indicates the efficiency of nucleotide coupling between the oligonucleotides of the first length and the second length.

This invention also is directed to methods of determining the extent to which a test condition causes deprotection of oligonucleotides synthesized on a substrate by spatially directed oligonucleotide synthesis. The method involves the steps of providing a substrate on which an ensemble of sequence-specific oligonucleotides has been synthesized, wherein the active sites on the free terminal nucleotides of the ensemble bear a protecting group; exposing an area of the substrate to the test condition, thereby exposing unprotected active sites from which protective groups have been removed; and determining the amount of unprotected active sites in the area. The amount indicates the extent to which the test condition caused removal of protective groups.

Also provided are methods of determining the extent of depurination of oligonucleotides synthesized on a substrate by spatially directed oligonucleotide synthesis. One method involves providing a substrate having a surface with linkers having an active site for oligonucleotide synthesis, the linkers being resistant to cleavage under cleavage conditions; synthesizing an ensemble of sequence-specific oligonucleotides in an area of the substrate, the oligonucleotides having active sites for attaching a detectable label; attaching a detectable label to the oligonuleotides in the ensemble; exposing the ensemble to a test condition; exposing the ensemble to cleavage conditions that cause cleavage of depurinated oligonucleotides; and determining the amount of detectable label in the area.

The other method for testing extent of depurination involves providing a substrate having a surface with linkers having an active site for oligonucleotide synthesis, the linkers being resistant to cleavage under cleavage conditions; synthesizing an ensemble of sequence-specific oligonucleotides in an area of the substrate by spatially directed oligonucleotide synthesis under a test condition, the oligonucleotides having active sites for attaching a detectable label; attaching a detectable label to the active sites; exposing the ensemble to cleavage conditions that cause cleavage of depurinated oligonucleotides; and determining the amount of detectable label in the area.

Another method of this invention is for determining whether an ensemble of oligonucleotides synthesized on a substrate by spatially directed oligonucleotide synthesis contains double-stranded nucleic acids. The method involves providing a substrate on which an ensemble of sequence-specific oligonucleotides has been synthesized in an area of the substrate, the oligonucleotides bearing a detectable label that is released upon cleavage of the oligonucleotide; contacting the ensemble with an agent that cleaves double-stranded nucleic acids, thereby releasing from the substrate detectable label attached to cleaved, double-stranded nucleic acids; and determining the amount of detectable label in the area. The amount of detectable label is inversely related to the amount of double-stranded nucleic acids.

In one embodiment of these methods, spatially directed nucleotide coupling is performed by light-directed nucleotide coupling. In the methods of this invention the step of detecting the amount of certain oligonucleotides on a substrate can involve attaching a detectable label to oligonucleotides in the array. The label can be a fluorescent label, a chemi-luminescent label, a bio-luminescent label, a colorimetric label or a light-scattering label.

DETAILED DESCRIPTION OF THE INVENTION

I. General

This invention provides methods for optimizing the production, storage and use of oligonucleotide arrays produced by spatially directed oligonucleotide synthesis and, in particular, light-directed oligonucleotide synthesis. The methods involve testing arrays produced under a variety of conditions used in the preparation of substrates, the synthesis of nucleic acids on those substrates and the post-production handling, storage, shipment or use of the manufactured biological chips. The invention also provides the ability to test many conditions on a single chip, allowing greater control over the testing process. Also, the ability to test a variety of combinations of conditions on a single chip provides increased flexibility and screening capacity. As used in quality control procedures for manufacturing oligonucleotide arrays, the methods can involve manufacturing the arrays in high volume, and testing selected arrays for various quality parameters such as nucleotide coupling efficiency; amount of deprotection of oligonucleotides; oligonucleotide integrity, e.g., amount of depurination; or amount of double stranded oligonucleotides in the array. Manufacturing arrays in high volume means manufacturing at least 10, 50, 500, 1000, 2000, 5000 or 10,000 oligonucleotide arrays per day from a single fabricating machine or in a single fabrication facility.

As used herein, "spatially directed oligonucleotide synthesis" refers to any method of directing the synthesis of an oligonucleotide to a specific location on a substrate. Methods for spatially directed oligonucleotide synthesis include, without limitation, light-directed oligonucleotide synthesis, microlithography, application by ink jet, microchannel deposition to specific locations and sequestration with physical barriers. In general these methods involve generating active sites, usually by removing protective groups; and coupling to the active site a nucleotide which, itself, optionally has a protected active site if further nucleotide coupling is desired.

Figure 1:
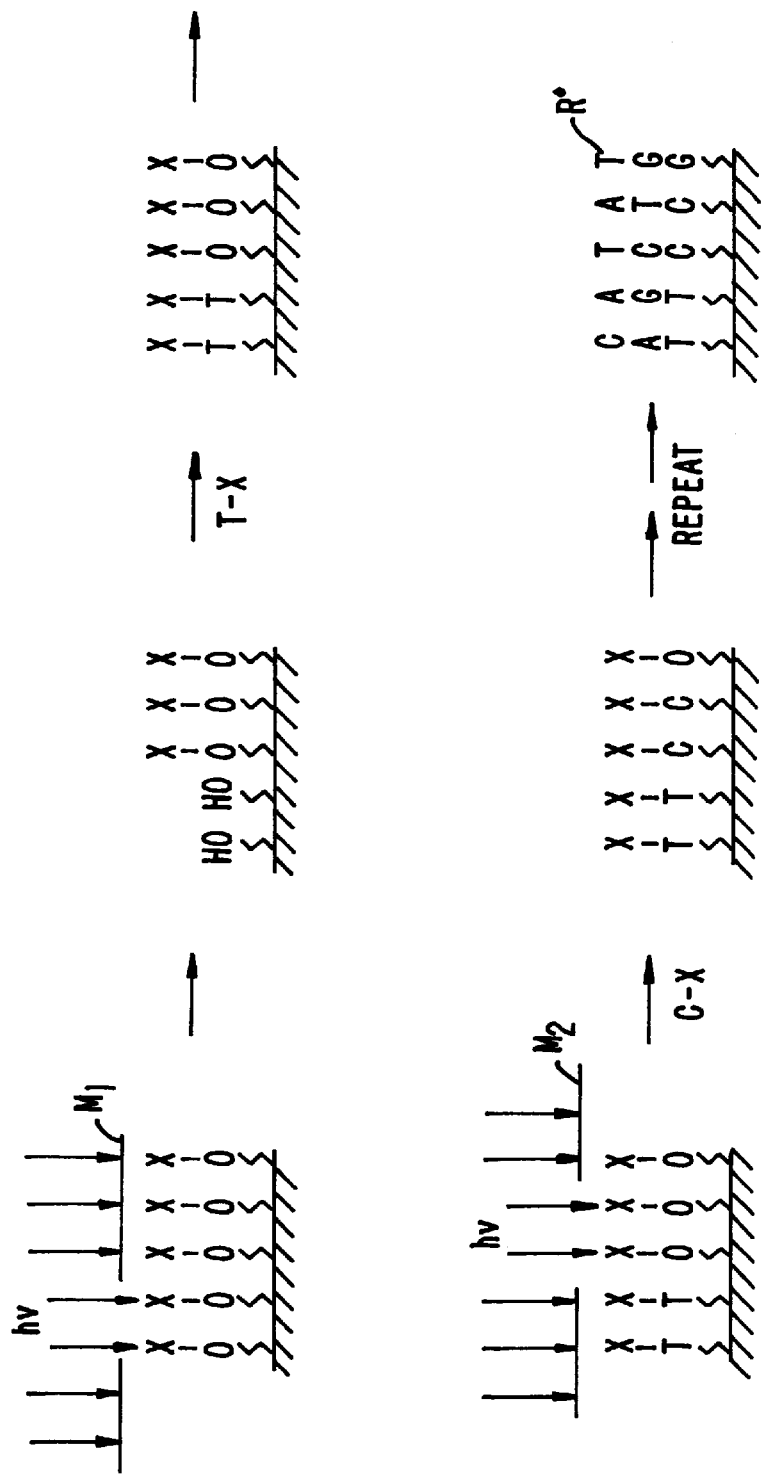
FIG. 1 depicts a general scheme for light-directed oligonucleotide synthesis.

In one embodiment oligonucleotide arrays are synthesized at specific locations by light-directed oligonucleotide synthesis. The pioneering techniques of this method are disclosed in U.S. Pat. No. 5,143,854; PCT WO 92/10092; PCT WO 90/15070; U.S. Pat. No. 5,571,639 and U.S. patent application Ser. Nos. and Ser. Nos. 07/624,120, and 08/082, 937, incorporated herein by reference for all purposes. The basic strategy of this process is outlined in FIG. 1. The surface of a solid support modified with linkers and photolabile protecting groups (⎯O—X) is illuminated (hv) through a photolithographic mask (M$_j$), yielding reactive hydroxyl groups (HO) in the illuminated regions. A 3'-O-phosphoramidite-activated deoxynucleoside (protected at the 5'-hydroxyl with a photolabile group, TX) is then presented to the surface and coupling occurs at sites that were exposed to light. Following the optional capping of unreacted active sites and oxidation, the substrate is rinsed and the surface is illuminated (hv) through a second mask (M$_2$), to expose additional hydroxyl groups for coupling to the linker. A second 5'-protected, 3'-O-phosphoramidite-activated deoxynucleoside (CX) is presented to the surface. The selective photodeprotection and coupling cycles are repeated until the desired set of products is obtained. Photolabile groups are then optionally removed and the sequence is, thereafter, optionally capped. Side chain protective groups, if present, are also removed. Since photolithography is used, the process can be miniaturized to generate high-density arrays of oligonucleotide probes. Furthermore, the sequence of the oligonucleotides at each site is known.

This general process can be modified. For example, the nucleotides can be natural nucleotides, chemically modified nucleotides or nucleotide analogs, as long as they have activated hydroxyl groups compatible with the linking chemistry. The protective groups can, themselves, be photolabile. Alternatively, the protective groups can be labile under certain chemical conditions, e.g., acid. In this example, the surface of the solid support can contain a composition that generates acids upon exposure to light. Thus, exposure of a region of the substrate to light generates acids in that region that remove the protective groups in the exposed region. Also, the synthesis method can use 3'-protected 5'-0-phosphoramidite-activated deoxynucleoside. In this case, the oligonucleotide is synthesized in the 5' to 3' direction, which results in a free 5' end.

The general process of removing protective groups by exposure to light, coupling nucleotides (optionally competent for further coupling) to the exposed active sites, and optionally capping unreacted sites is referred to herein as "light-directed nucleotide coupling."

Another method of spatially directed oligonucleotide synthesis involves mechanically directing nucleotides to specific locations on a substrate for coupling, for example, by ink jet technology. Ink jets currently can apply material to specific locations in areas as small as 200 square microns in diameter. (See, e.g., U.S. Pat. No. 5,599,695, incorporated herein by reference.)

Another method of spatially directed oligonucleotide synthesis involves directing nucleotides to specific locations on a substrate for coupling by the use of microchannel devices. Microchannel devices are described in more detail in International application WO 93/09668, incorporated herein by reference.

Another method of spatially directed oligonucleotide synthesis involves directing nucleotides to specific locations on a substrate for coupling by the use of physical barriers. In this method, a physical barrier is applied to the surface such that only selected regions are exposed to the conditions during polymer chain extension. For example, the surface of a chip may be coated with a material that can be removed upon exposure to light. After exposing a particular area to light, the material is removed, exposing the surface of the chip for nucleotide coupling. The exposed surface in this area can be exposed to the nucleotide, while the other areas or regions of the chip are protected. Then, the exposed area is re-covered, and protected from subsequent conditions until re-exposure. See, e.g., WO 93/09668, incorporated herein by reference.

Methods of spatially directed synthesis can be used for creating arrays of other kinds of molecules as well, and these arrays also can be tested by the methods of this invention. For example, using the strategies described above, spatially patterned arrays can be made of any molecules whose synthesis involves sequential addition of units. This includes polymers composed of a series of attached units and molecules bearing a common skeleton to which various functional groups are added. Such polymers include, for example, both linear and cyclic polymers of nucleic acids, polysaccharides, phospholipids, and peptides having either α-, β-, or ω-amino acids, heteropolymers in which a known drug is covalently bound to any of the above, polyurethanes, polyesters, polycarbonates, polyureas, polyamides, polyethyleneimines, polyarylene sulfides, polysiloxanes, polyimides, polyacetates, or other polymers which will be apparent to anyone skilled in the art. Molecules bearing a common skeleton include benzodiazepines and other small molecules, such as described in U.S. Pat. No. 5,288,514, incorporated herein by reference.

II. Appearance of a Structural Feature During Oligonucleotide Synthesis

A general method of this invention is directed to determining the extent to which a test condition causes the appearance of a structural feature in oligonucleotides produced on an oligonucleotide array by spatially directed oligonucleotide synthesis. This method involves providing a substrate having a surface with linkers having an active site for oligonucleotide synthesis. An ensemble of sequence-specific oligonucleotides is synthesized on the substrate by spatially directed oligonucleotide synthesis. The oligonucleotides can be provided with active sites for attaching a detectable label. The area is exposed to the test condition. Then, the amount of oligonucleotides having the structural feature is determined.

III. Coupling Efficiency

Figure 2:
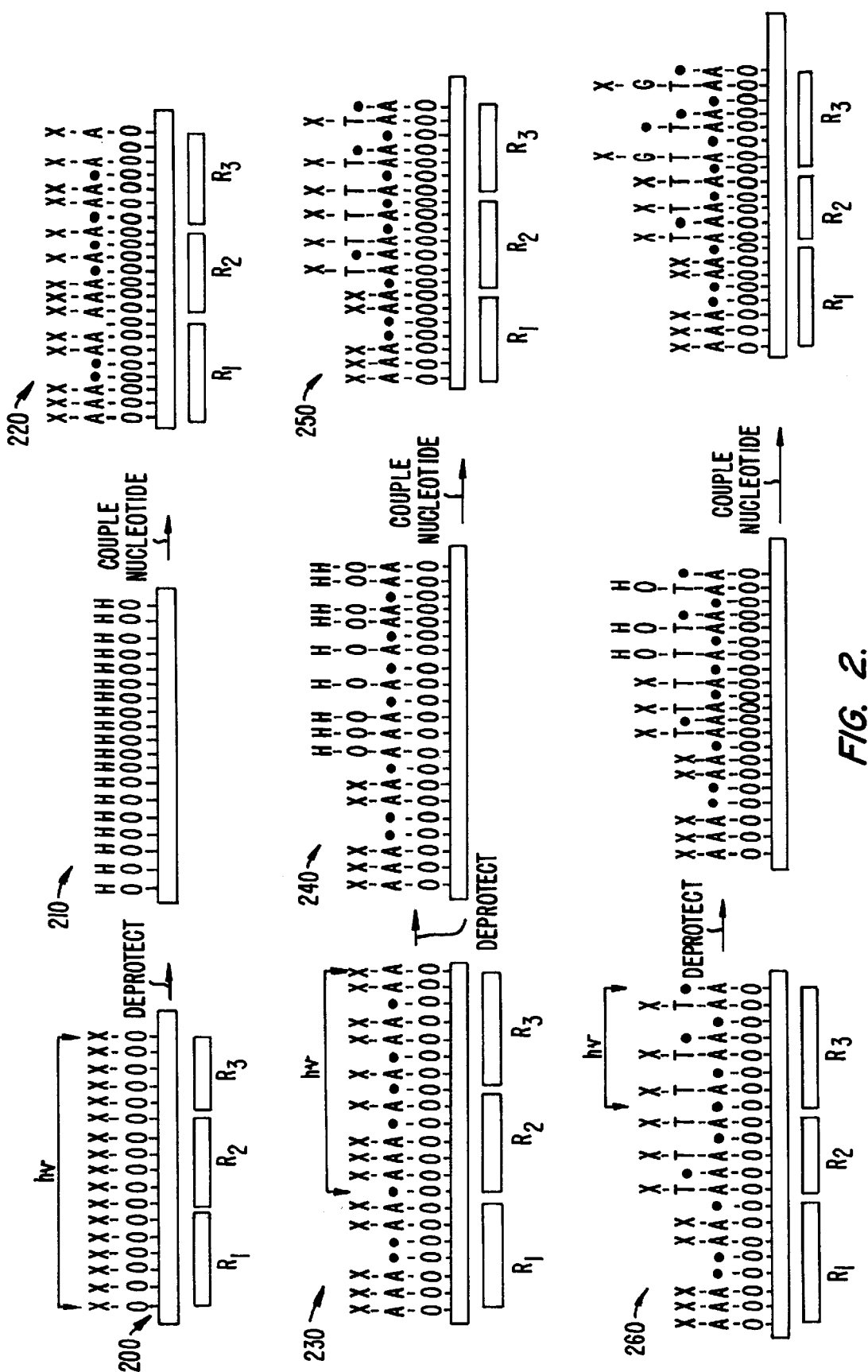
FIG. 2 depicts an embodiment of this invention useful for determining the efficiency of coupling reactions in oligonucleotide synthesis.

One method of this invention is directed to testing the efficiency of nucleotide coupling in the synthesis of an oligonucleotide array. This method is useful in optimizing conditions for chip synthesis and for testing bulk production processes. Referring to FIG. 2, the method involves the following steps. A substrate is provided having a surface with linkers having active sites for coupling nucleotides or other monomers (200). First nucleotides (at least one but optionally more, e.g., "A") are coupled to active sites in a first area (R$_1$) and at least one second area (R$_2$, and in this example, R$_3$) of the substrate by spatially directed nucleotide coupling, e.g., by exposure to light (hv).

More specifically, protective groups, "X," are removed from linkers in the region to expose the active sites, "OH" (210). The active sites are exposed to protected nucleotides, "A," for coupling. If coupling is not 100% efficient, areas R$_1$, R$_2$ and R$_3$ will contain some proportion of the linkers having terminal nucleotides, i.e., "A," which are competent for additional coupling and some proportion of the linkers having unreacted, unprotected active sites. The unreacted, unprotected active sites in all the areas are capped (220). In FIG. 2, capped active sites are designated by: "•". Reagents are then washed from the chip.

Then, in at least one second area of the chip, (e.g., R$_2$ and R$_3$) second nucleotides, (e.g., "T") are coupled to the uncapped linkers by spatially directed nucleotide coupling. Again, protective groups, "X," are removed from linkers, (230), in these areas to produce reactive groups, "OH" (240). The reactive groups are exposed to protected nucleotides, "T," for coupling. Any unreacted active sites in the second areas are capped and reagents are then washed from the chip. Thus, in areas R$_2$ and R$_3$, if coupling has not been 100% efficient, some proportion of the linkers are capped, some proportion end with a capped "A" and some proportion end with competent "AT" (250).

This process can be continued for any number of subsequent rounds of nucleotide coupling to subsequent areas. To follow the process one step further, third nucleotides (e.g., "G") are attached to a subsequent area (here, $R_3$) by another round of nucleotide coupling (260, 270). If coupling has not been 100% efficient, the subsequent area ($R_3$) will have capped linkers, linkers ending in capped "A," capped "AT" and competent "ATG" (280).

After at least two rounds of nucleotide coupling, the chip can be tested for coupling efficiency. This testing involves determining the amounts of competent, uncapped active sites in any two areas of the substrate. Then, the amounts are compared, thereby providing the efficiency of nucleotide coupling between the two areas.

For example, comparing the amounts of uncapped active sites in any area and any immediately subsequent area (e.g., $R_1$ and $R_2$, or $R_2$ and $R_3$) provides the coupling efficiency of the coupling step in the subsequent area. Comparing the amounts of uncapped active sites in the first area ($R_1$) and the final area to which nucleotides were coupled ($R_3$) provides the overall efficiency of the entire oligonucleotide synthesis.

Even in its simplest form, with only a single coupling step, the presence of active sites in area $R_1$ after this procedure gives evidence that the coupling was at least partially successful. If the nucleotide monomer was added in a spatially-defined manner, the resulting pattern of labelled and unlabelled areas can also be used to estimate the contrast and resolution of the patterning method.

The amount of uncapped active sites in an area can be determined by any quantification method known in the art. In a preferred embodiment, the uncapped ("competent") active sites are labeled with a detectable label, and the amount of label in an area is determined. Methods of coupling detectable labels to active sites and quantifying the amount of label are useful in other methods of this invention, as well. The detectable label can be, for example, a luminescent label, a light scattering label, a radioactive label, or a label made detectable by reaction with an enzyme.

Figure 3:
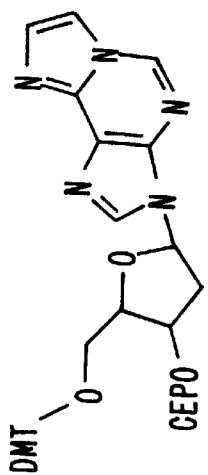
FIG. 3 shows the fluorescent tags: 1) etheno-dA and 2) fluorescein.
Figure 3:
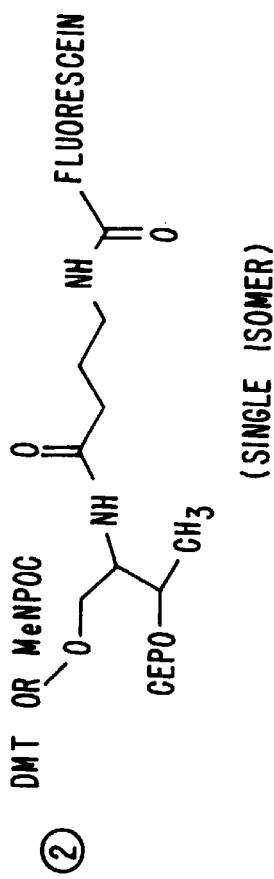
Figure 3:
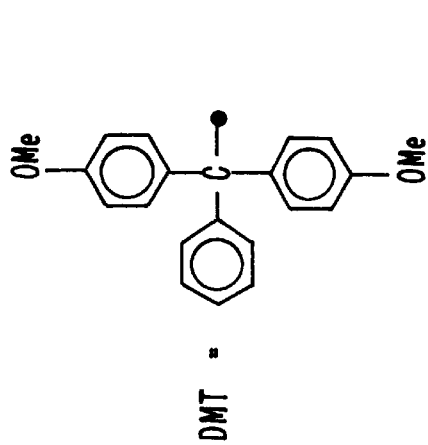
Figure 3:
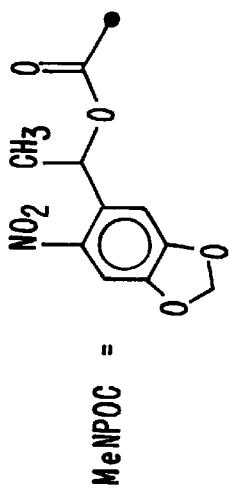
Figure 3:
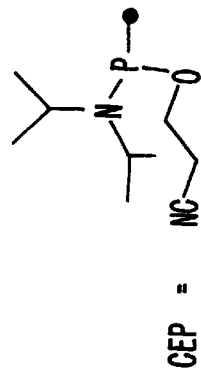

Preferably, the detectable label is a luminescent label. Useful luminescent labels include fluorescent labels, chemi-luminescent labels, bio-luminescent labels, and colorimetric labels, among others. Most preferably, the label is a fluorescent label such as a fluorescein, a rhodamine, a polymethine dye derivative, a phosphor, and so forth. Commercially available fluorescent labels include, inter alia, fluorescein phosphoramidites such as Flureprime (Pharmacia, Piscataway, N.J.), Fluoredite (Millipore, Bedford, Mass.) and FAM (ABI, Foster City, Calif.). Examples of fluorescent labels are shown in FIG. 3.

To label the active sites, the protective groups in an area are first removed, exposing the active sites. The area of the substrate is exposed to the activated fluorescent phosphoramidite, which reacts with all of the deprotected 5'-hydroxyl groups. Then the area is exposed to an alkaline solution (e.g., 50% ethylenediamine in ethanol for 1–2 hours at room temperature). This is necessary to remove the protecting groups from the fluorescein tag.

To avoid self-quenching interactions between fluorophores on the surface of a biological chip, the fluorescent tag monomer should be diluted with a non-fluorescent analog of equivalent reactivity. For example, in the case of the fluorescein phosphoramidites noted above, a 1:20 dilution of the reagent with a non-fluorescent phosphoramidite such as the standard 5'-DMT-nucleoside phosphoramidites, has been found to be suitable. Correction for background non-specific binding of the fluorescent reagent and other such effects can be determined by routine testing. From an image of the surface fluorescence, one can determine the extent of detection by the intensity of surface fluorescence in the regions subjected to the test conditions relative to that elsewhere on the surface.

Useful light scattering labels include large colloids, and especially the metal colloids such as those from gold, selenium and titanium oxide.

Radioactive labels include, for example, $^{32}p$. This label can be detected by a phosphoimager. Detection, of course, depends on the resolution of the imager. Phosophoimagers are available having resolution of 50 microns. Accordingly, this label is currently useful with chips having features of at least that size.

Figure 4:
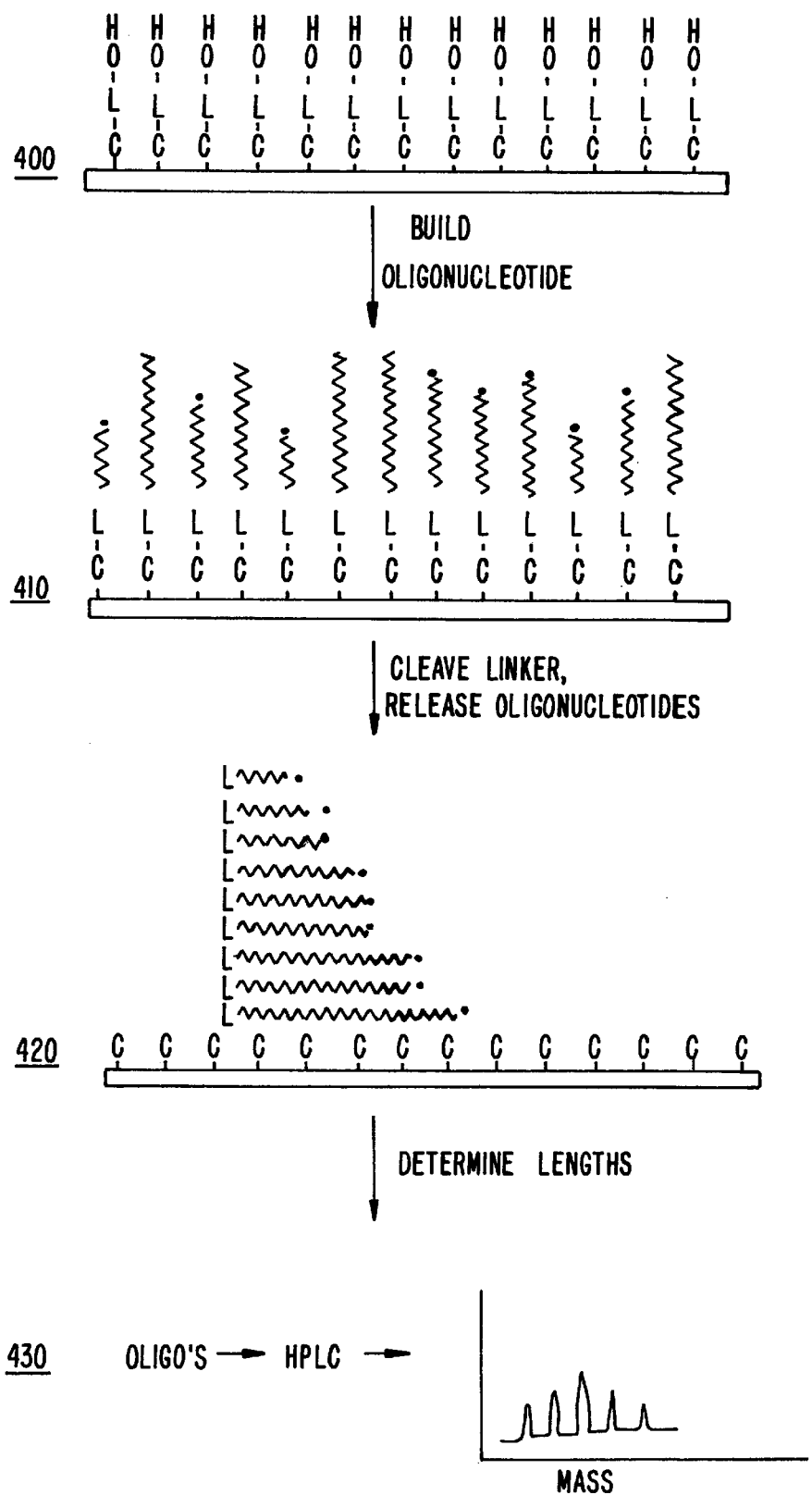
FIG. 4 depicts an embodiment of this invention useful for determining the efficiency of coupling reactions in oligonucleotide synthesis in which oligonucleotides are released from the substrate by cleaving a cleavable linker.
Figure 5:
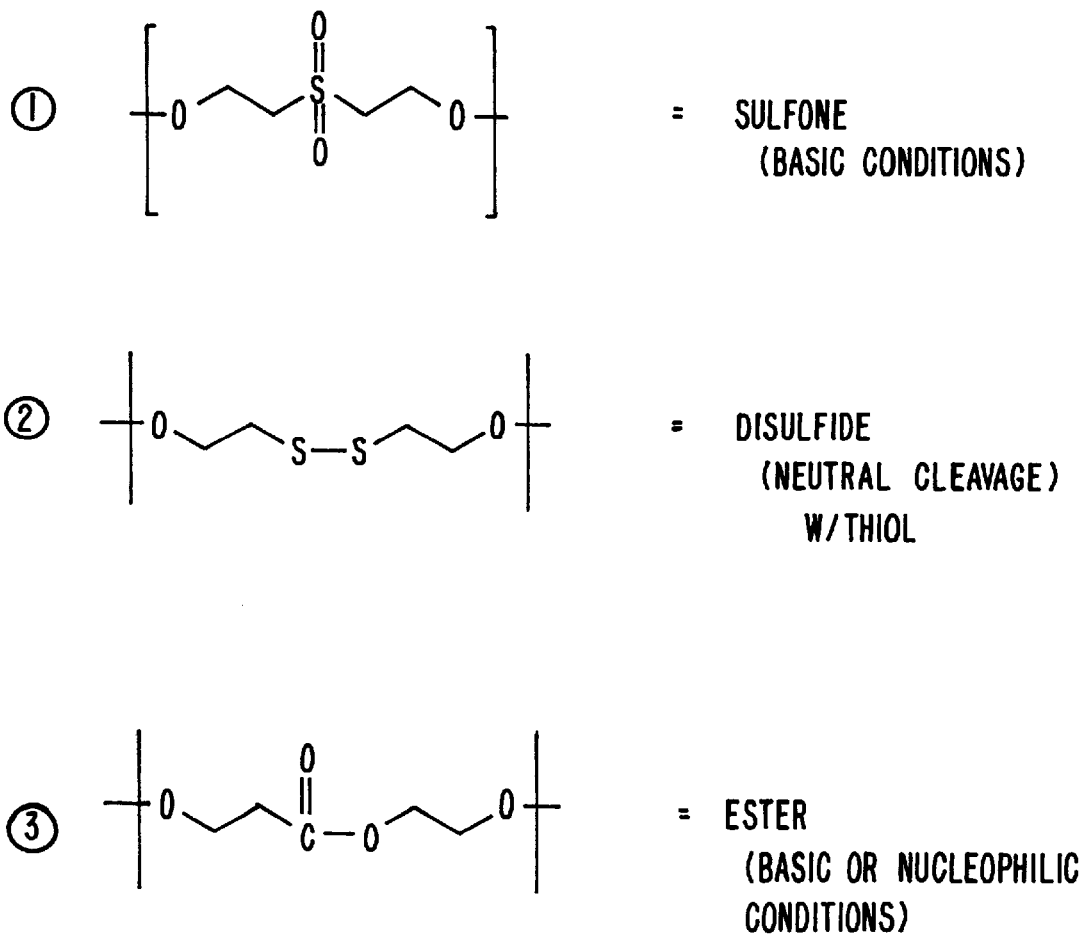
FIG. 5 depicts the cleavable linkers 1) sulfone, 2) disulfide and 3) ester.

Another method of determining the efficiency of nucleotide coupling in the synthesis of an oligonucleotide array, depicted in FIG. 4, involves separating and quantifying oligomers on the basis of length. Referring to FIG. 4, a substrate is provided having a surface with cleavable linkers ("C") including a detectable label ("L") and an active site ("OH") for nucleotide coupling (400). Linkers can be used that cleave under acidic, basic, oxidative, reductive or photolytic conditions. For example, the cleavable linker can be a sulfone (cleavable under basic conditions), a disulfide (cleavable by reducing conditions) or an ester (cleavable under basic or nucleophilic conditions) (see FIG. 5).

Then, at least one nucleotide is coupled to the active sites by spatially directed oligonucleotide synthesis and the unreacted, unprotected active sites are capped after at least one coupling step. If coupling has not been 100% efficient, the substrate will have oligonucleotides of various lengths (410).

Figure 6:
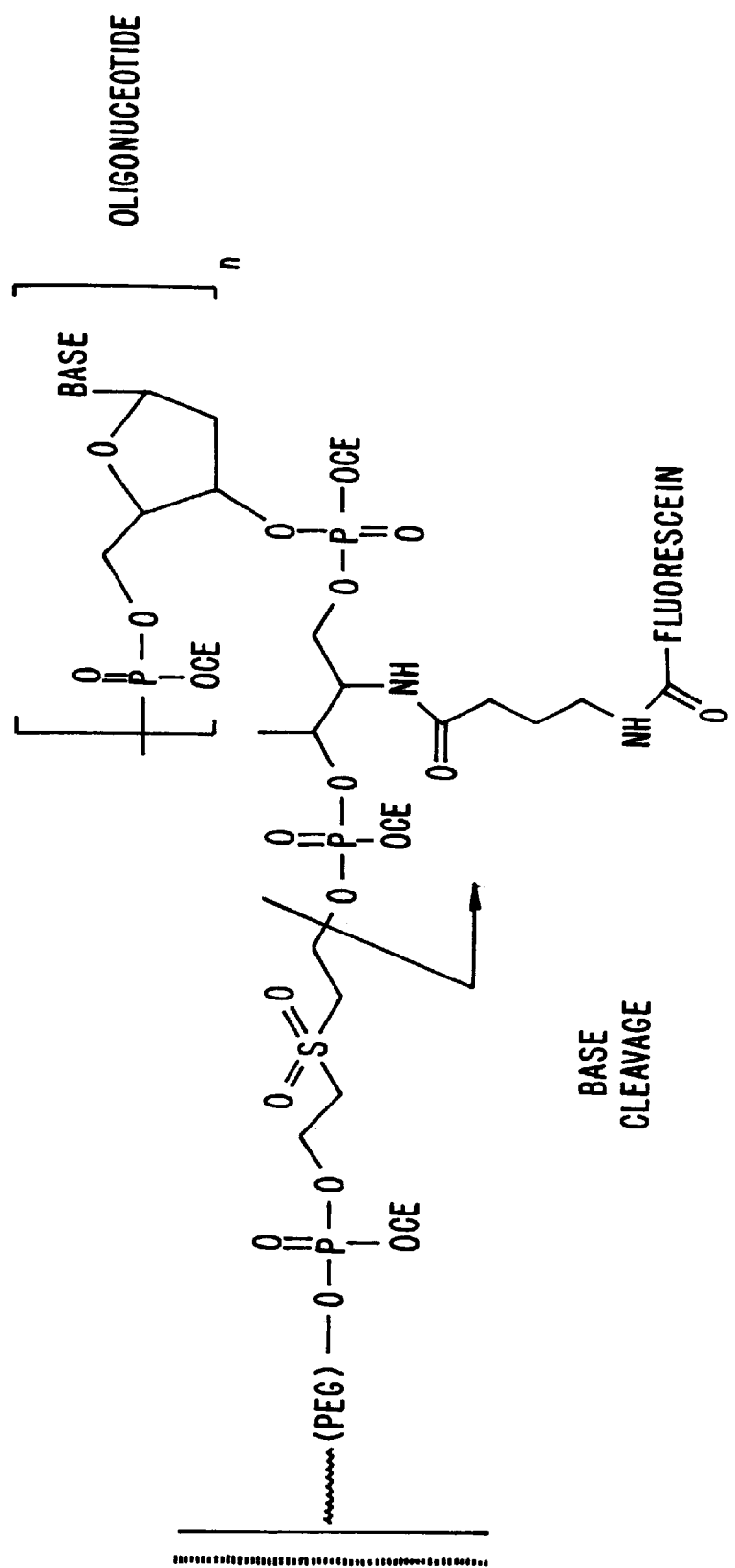
FIG. 6 provides a specific scheme for attaching an oligonucleotide through a detectably labeled building block attached to a surface through a cleavable linker.

Then the substrate is exposed to conditions that cleave the linker. (See, e.g., FIG. 6.) All of the nucleic acid products which are released carry the detectable label at one end (420). The purpose of the tag is to enhance detection of the oligomers, since they may not be easily detectable otherwise. Also, typical substrate synthesis site densities are such that the cleaved products may only be recoverable in minute quantities, and this further necessitates the inclusion of the tag to increase sensitivity.

Then, the length of the released oligonucleotides is determined (430). In one embodiment, the mixture of cleaved products is analyzed by a method capable of separating and quantifying oligomers on the basis of length. The preferred separation method is HPLC (reverse-phase or anion exchange), and the preferred tag would be either a chromophore with a large absorption coefficient, or a fluorophore with a large absorption coefficient and fluorescence quantum yield.

Then, the amounts of oligonucleotides having a first and a second length are compared. The comparative amount indicates the efficiency of nucleotide coupling between the oligonucleotides of the first length and the second length.

IV. Deprotection Efficiency

Figure 7:
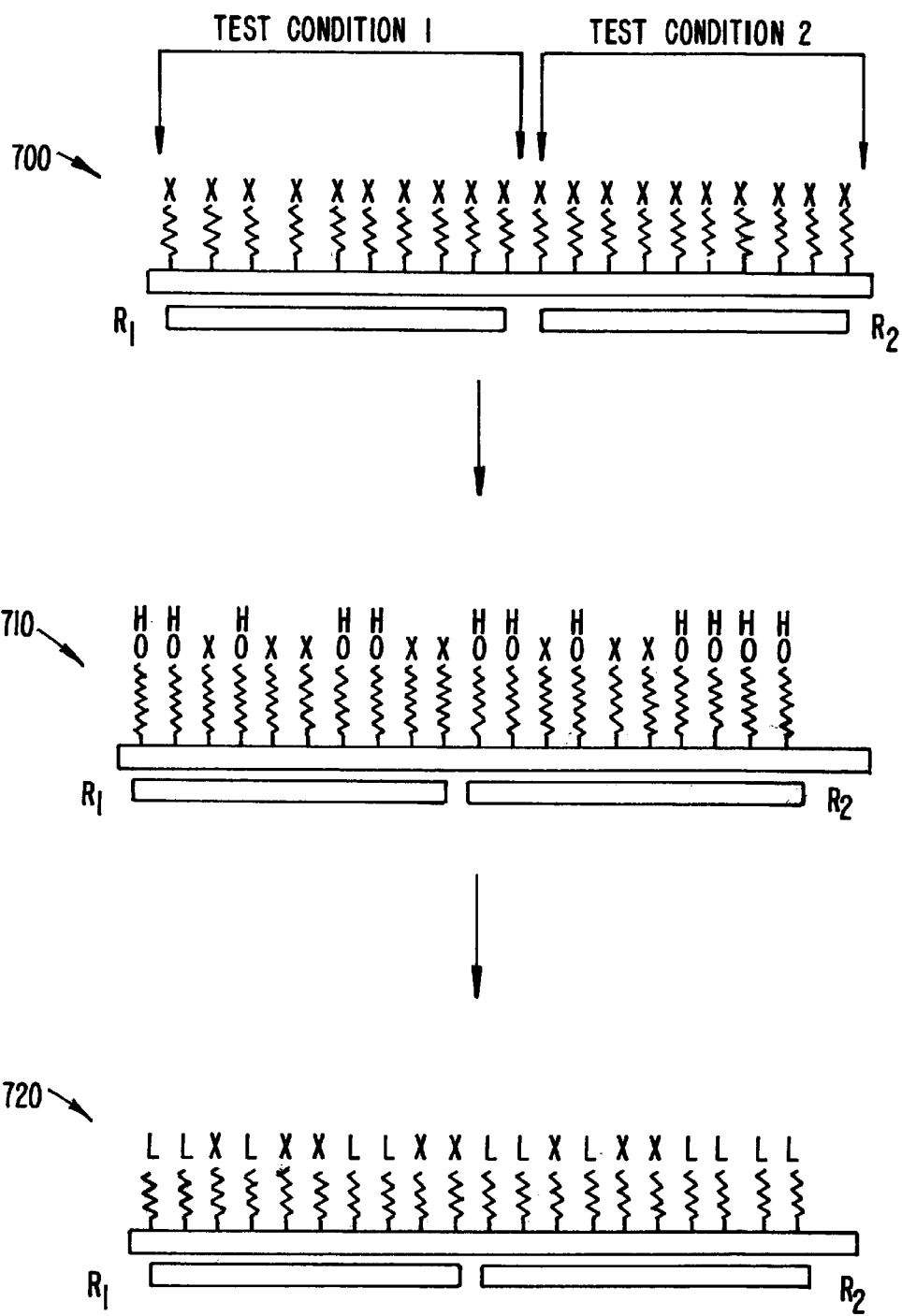
FIG. 7 depicts an embodiment of this invention useful for testing deprotection of an oligonucleotide attached to an oligonucleotide array.

Another method of this invention is directed to testing the extent to which a test condition causes deprotection of an ensemble of sequence-specific oligonucleotides synthesized on an oligonucleotide array. This method is useful for optimizing deprotection methods during synthesis, as well as testing the extent to which certain conditions, e.g., storage conditions, cause deprotection of oligonucleotide arrays. Referring to FIG. 7, the method involves the following steps. A substrate is provided on which an ensemble of sequence-specific oligonucleotides has been synthesized by spatially directed oligonucleotide synthesis (700). The active sites on the free terminal nucleotide of the ensemble bear a protecting group ("X"). An area of the substrate ("$R_1$") is then exposed to a test condition. Another area ("$R_2$") can be exposed to a different test condition. After exposure to the test condition, the substrate is washed, exposing any unprotected active sites ("OH") on nucleotides from which the protective group has been removed (710). The amount of unprotected active sites is determined in the area. The amount indicates the extent to which the test condition caused removal of protective groups.

In a preferred embodiment of this method, the amount of deprotected active sites is determined by exposing the ensemble of oligonucleotide molecules to a detectable label ("L") for coupling to deprotected active sites (720), and determining the amount of detectable label in the area. Preferably, the detectable label is a fluorescent marker. Methods of coupling detectable labels to deprotected active sites are described above.

In one embodiment of this method, a substrate is provided on which at least two ensembles of different sequence-specific oligonucleotides have been synthesized by spatially directed oligonucleotide synthesis, and at least two areas of the substrate, each area having different sequence-specific oligonucleotides, are exposed to the same test condition.

Conditions to test for deprotection include, for example, chemical reagents used in synthesis, e.g., exposure to light, acid, base, nucleophilic agent, reducing agent or oxidizing agent.

V. Rates of Depurination

Figure 8:
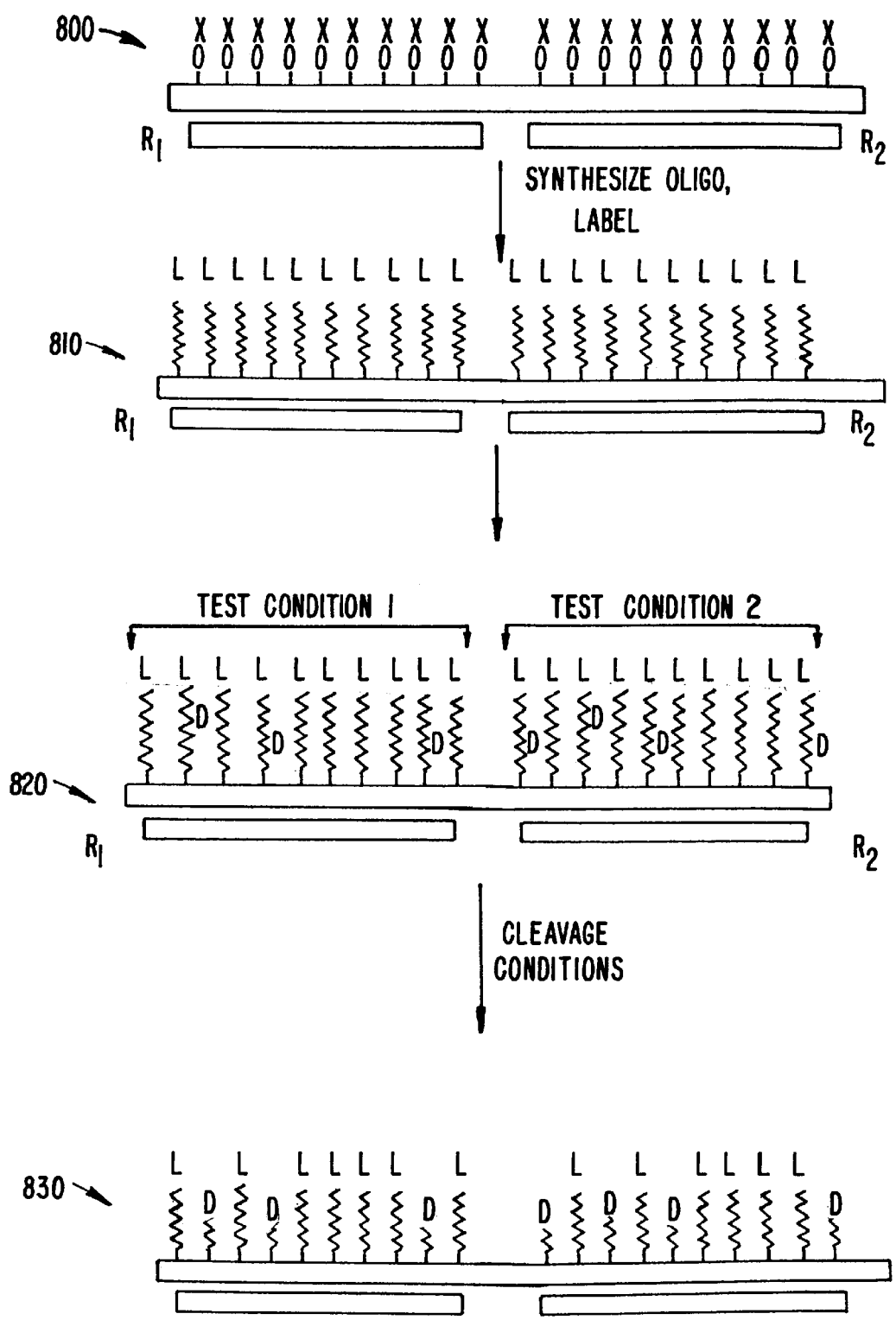
FIG. 8 depicts an embodiment of this invention useful for testing the ability of a test condition to depurinate oligonucleotides in an array.

Another method of this invention is directed to testing the extent of depurination of oligonucleotides synthesized on a substrate. Depurinated oligonucleotides are prone to backbone cleavage when exposed to alkaline conditions. Referring to FIG. 8, a substrate is provided having a surface with linkers having an active site for coupling nucleotides (800). The linkers are to be resistant to cleavage under alkaline conditions. An ensemble of sequence-specific oligonucleotides having active sites for the attachment of a detectable label is synthesized in an area of the substrate ("$R_1$") by spatially directed oligonucleotide synthesis. An ensemble of oligonucleotides having the same sequence or a different sequence can be synthesized in a second area ("$R_2$"), as well. Then, a detectable label ("L") is attached to active sites (810). Methods of coupling detectable labels to deprotected active sites are described above.

Then, the ensemble the first area is exposed to the test condition to be tested for its ability to depurinate oligonucleotides. This may result in depurination ("D") of oligonucleotides in the ensemble (820). Also, if an ensemble in a second area has the oligonucleotides of the same sequence, it can be exposed to a different test condition, in order to test the effect of different conditions on the same oligonucleotide sequence. If an ensemble in a second area has oligonucleotides of a different sequence, it can be exposed to the same test condition, in order to test the effect of the same condition on different sequences.

Figure 10:
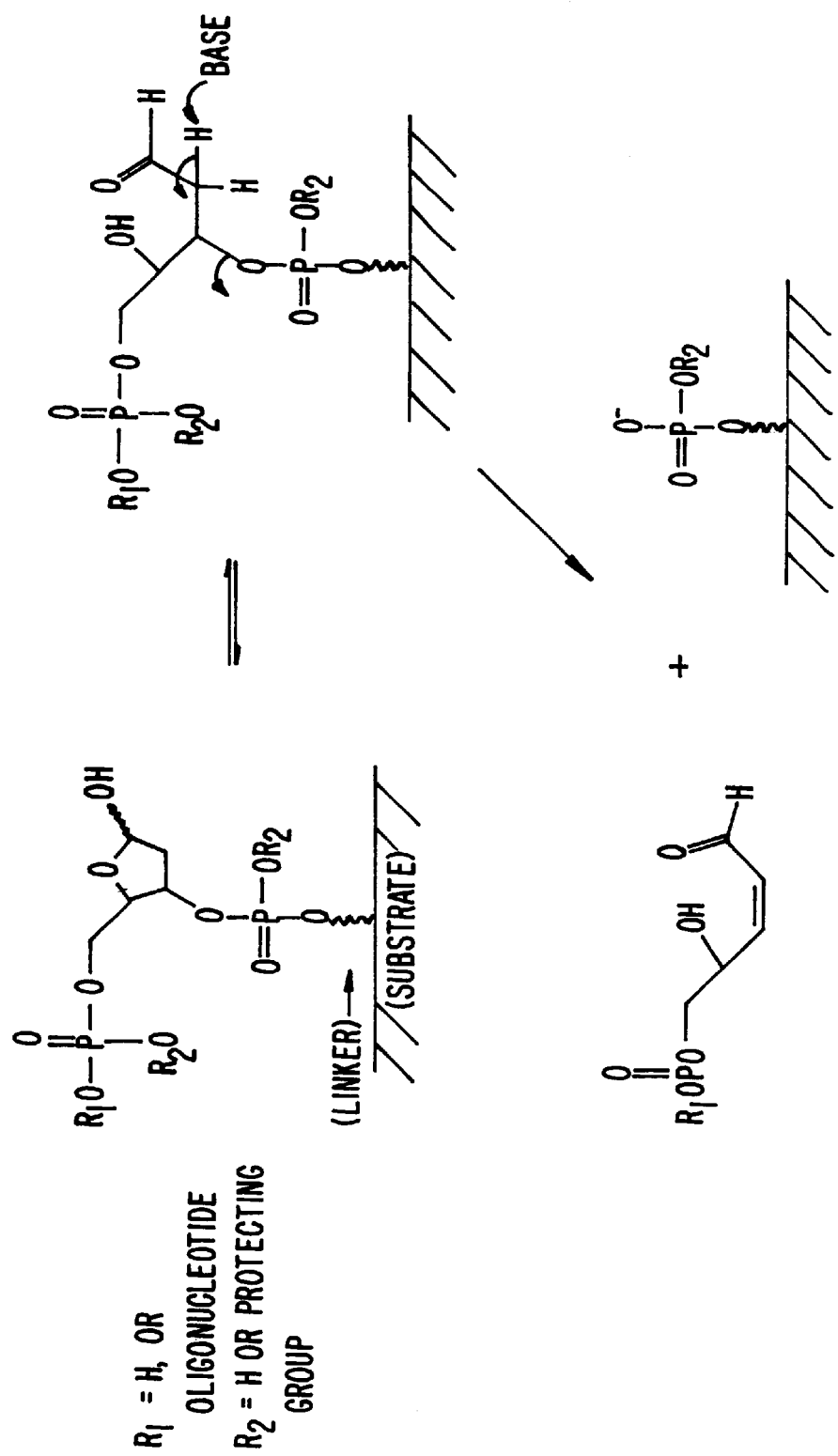
FIG. 10 shows a mechanism of base-catalyzed cleavage of oligonucleotides from abasic sites of a substrate.

The ensemble(s) is then exposed to cleavage conditions, i.e., conditions that cause cleavage of depurinated oligonucleotides. These conditions can be, e.g., alkaline conditions that tend to cause backbone cleavage of depurinated oligonucleotides, for example, 50% ethylenediamine in ethanol for 1–2 hours at room temperature. The mechanism of base-catalyzed cleavage of abasic sites in oligonucleotides is well-known and shown in FIG. 10. Strand cleavage at the depurination sites results in loss of the detectable label and also removes all protecting groups from all of the polymer species (830).

The amount of uncleaved oligonucleotides in the area is determined, preferably by imaging of the surface tag. This reveals depurination by a reduction in surface tag in the regions subjected to the test conditions relative to that elsewhere on the surface. The amount of depurination is inversely related to the amount of detectable label coupled to an ensemble.

Figure 9:
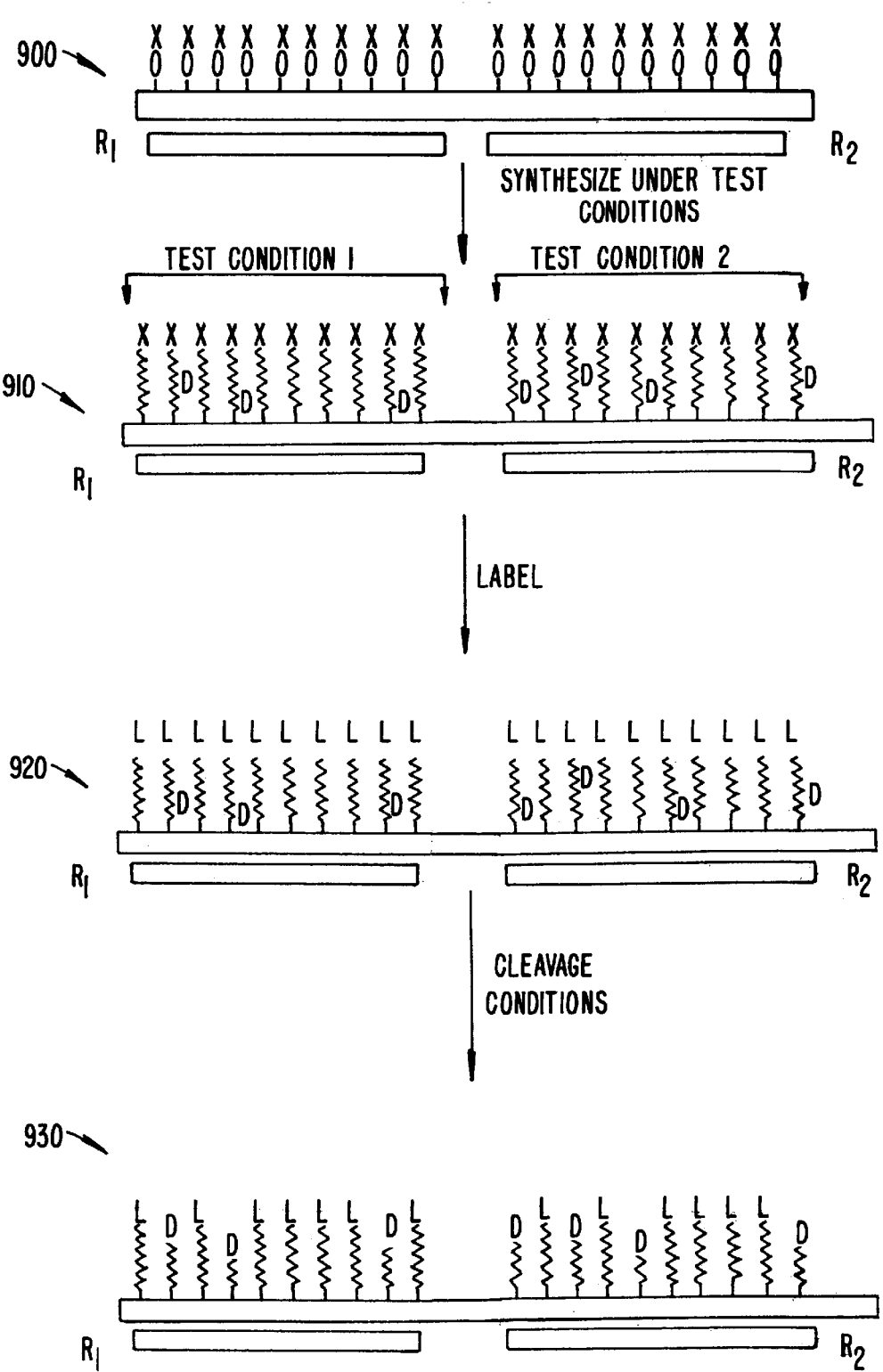
FIG. 9 depicts an embodiment of this invention useful for testing depurination of oligonucleotides during synthesis in an array.

In an alternative embodiment, the oligonucleotides are synthesized under a test condition, rather than exposing to the test condition after synthesis. Referring to FIG. 9, a substrate is provided having a surface with linkers having an active site for coupling nucleotides (900). The linkers are to be resistant to cleavage under alkaline conditions. An ensemble of sequence-specific oligonucleotides having active sites for the attachment of a detectable label is synthesized in an area of the substrate ("$R_1$") by spatially directed oligonucleotide synthesis using conditions to be tested for their ability to cause depurination of the oligonucleotides (910). An ensemble with a different nucleotide sequence also can be synthesized in a second area of the substrate ("$R_2$") using the same test conditions. Alternatively, an ensemble can be synthesized in a second area having the same nucleotide sequence using a different test condition. Then, a detectable label is attached to the active sites (920). The ensemble(s) is exposed to cleavage conditions. Again, this releases label from depurinated sites (930). Then, the amount of label in the area(s) is determined.

Various conditions used in the synthesis of a chip can be tested for the extent to which they cause depurination. For example, one method of making chips involves coating an area with a material that generates an acid upon exposure to light. Acids cause removal of acid-labile protective groups, but they also should be chosen not to cause depurination. Therefore, particular acids used in the production of chips can be tested by this method for the extent to which they cause depurination. For example, photo-acid generating ("PAG") polymer films having a photo-activatable acid, such as those used as photo-resists in the semi-conductor industry, can be applied to various areas of the substrate in order to test the effect of particular acids in the deprotection process.

VI. Formation of Double-Stranded Structures

The method of this invention for determining the extent of depurination takes advantage of the fact that depurinated oligonucleotides are subject to cleavage and, thereby, to detection. A broader application of this method involves determining whether oligonucleotides synthesized on a substrate have a cleavable structural feature. The method involves exposing the oligonucleotides to conditions that cleave molecules having the cleavable structural feature and detecting the amount of cleaved oligonucleotides. Because certain structural features, such as intra- or inter-molecular hydrogen bonding, may interfere with chip function, such methods are useful in evaluating results obtained from chips.

For example, depending on their sequence, oligonucleotides can assume a secondary structure in an array by hybridizing internally to form hairpin loops, or hybridizing with other nearby molecules in the array. Also, double-stranded structures can form when the array is exposed to a probe having a sequence that is complementary to a sequence in the array, and that hybridizes with oligonucleotides having that sequence. Such double-stranded structures can be cleaved by agents that cleave double-stranded nucleic acids.

Figure 11:
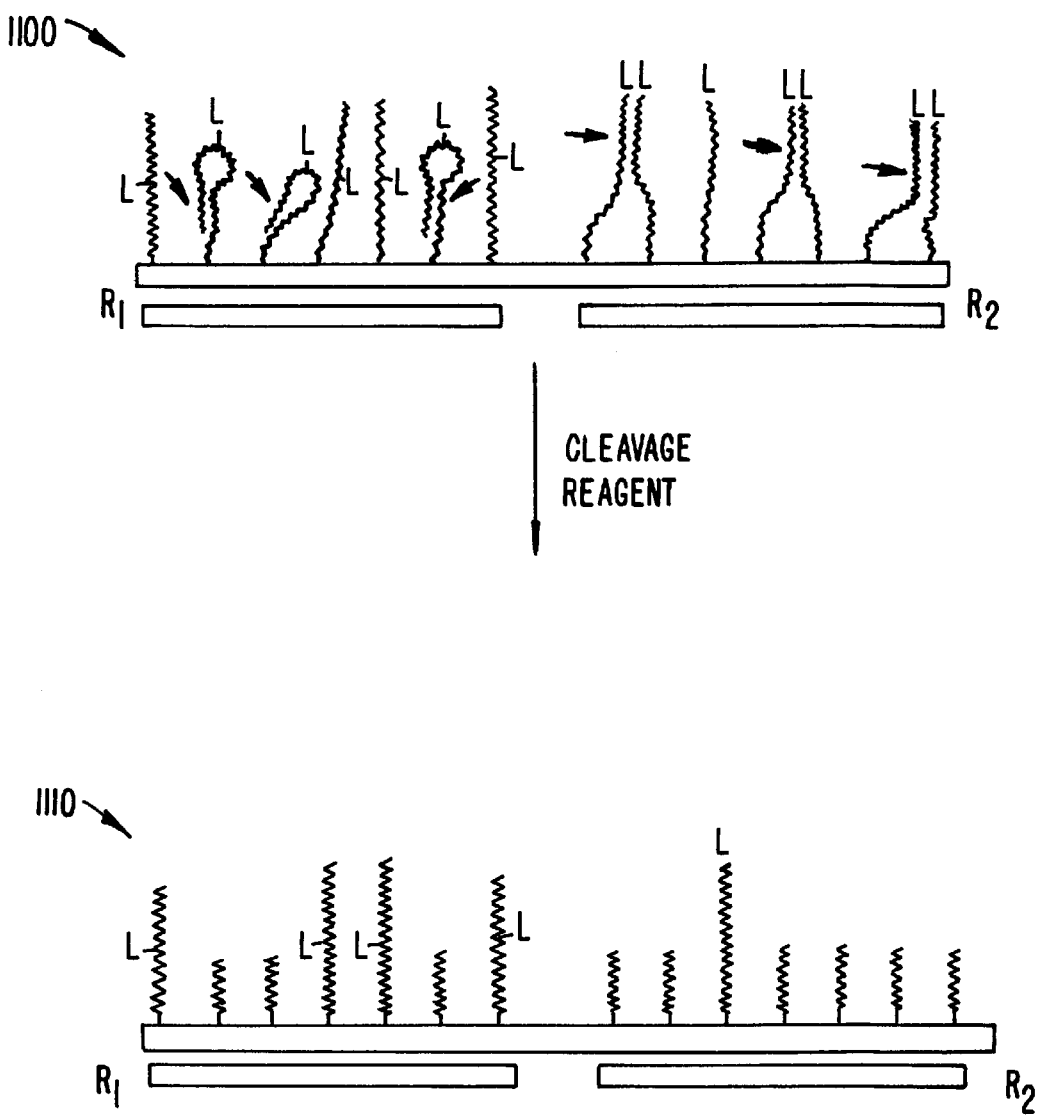
FIG. 11 depicts an embodiment of this invention useful for testing an oligonucleotide array for the presence of double-stranded structures.

Accordingly, this invention is directed to methods of determining whether an ensemble of oligonucleotides contains double-stranded structures. Referring to FIG. 11, the methods involve providing a substrate on which an ensemble of sequence-specific oligonucleotides has been synthesized in an area ("$R_1$") by spatially directed oligonucleotide synthesis (1100). The oligonucleotides in the ensemble bear a detectable label that is released upon cleavage of the oligonucleotide. The substrate can include a second area ("$R_2$") having a second ensemble of different sequence-specific oligonucleotides. In this example, the oligonucleotides in $R_1$ tend to form double-stranded structures within themselves, while the oligonucleotides in $R_2$ tend to form double-stranded structures between oligonucleotides in the ensemble. (Arrows in 1100 indicate potential double-stranded cleavage sites.)

The ensemble is then contacted with an agent that cleaves double-stranded nucleic acids, e.g., non-specific endonucleases or specific endonucleases, such as restriction enzymes. For example, if a specific sequence within the oligonucleotides is suspected of forming double-stranded structures, then a restriction endonuclease can be selected that recognizes and cleaves double-stranded nucleic acid molecules having the sequence. This releases from the substrate label attached to cleaved, double-stranded structures, leaving only label on uncleaved oligonucleotides (1110). Then, the amount of detectable label in the area is determined. The amount of label is inversely related to the amount of double-stranded structures in the area.

VII. Test Conditions

The methods of this invention are very versatile. A chip can have several ensembles of different sequence-specific oligonucleotides. Within any one ensemble, several sub-areas can be exposed to different test conditions. Thus, several different ensembles can be exposed to several different test conditions on a single chip. The oligonucleotide array can be exposed to one or more test conditions throughout the chip production process, or at specific times. The test conditions can change during the production process. Exposing different ensembles to the same condition is useful to test the effect of a condition on particular oligonucleotide sequences. Exposing ensembles of oligonucleotides to different conditions assists in identifying the effect of a condition on the manufacturing process.

The conditions to be tested by the methods of this invention are at the discretion of the practitioner. However, usually the practitioner will select conditions to be tested for the manufacturing process. These can include, for example, light, temperature, humidity, mechanical stress, reagents used in the synthesis, storage conditions, transportation conditions and operation conditions.

Many conditions involved with the chemistry of nucleotide coupling can be tested. These conditions can include, without limitation, identity and concentration of solvents and substrates used for deprotection, coupling and washing, wavelength and intensity of light applied during light-directed nucleotide coupling, and time of exposure to a condition. Of course, conditions can be applied to specific locations, or specific oligonucleotides can be synthesized at particular locations and the entire substrate can be subject to a test condition to determine the effect at each area.

VIII. Signal Detection and Interpretation

Determining a signal generated from a detectable label on a chip requires an oligonucleotide array reader. The nature of the oligonucleotide array reader depends upon the particular type of label attached to the target molecules.

Figure 12:
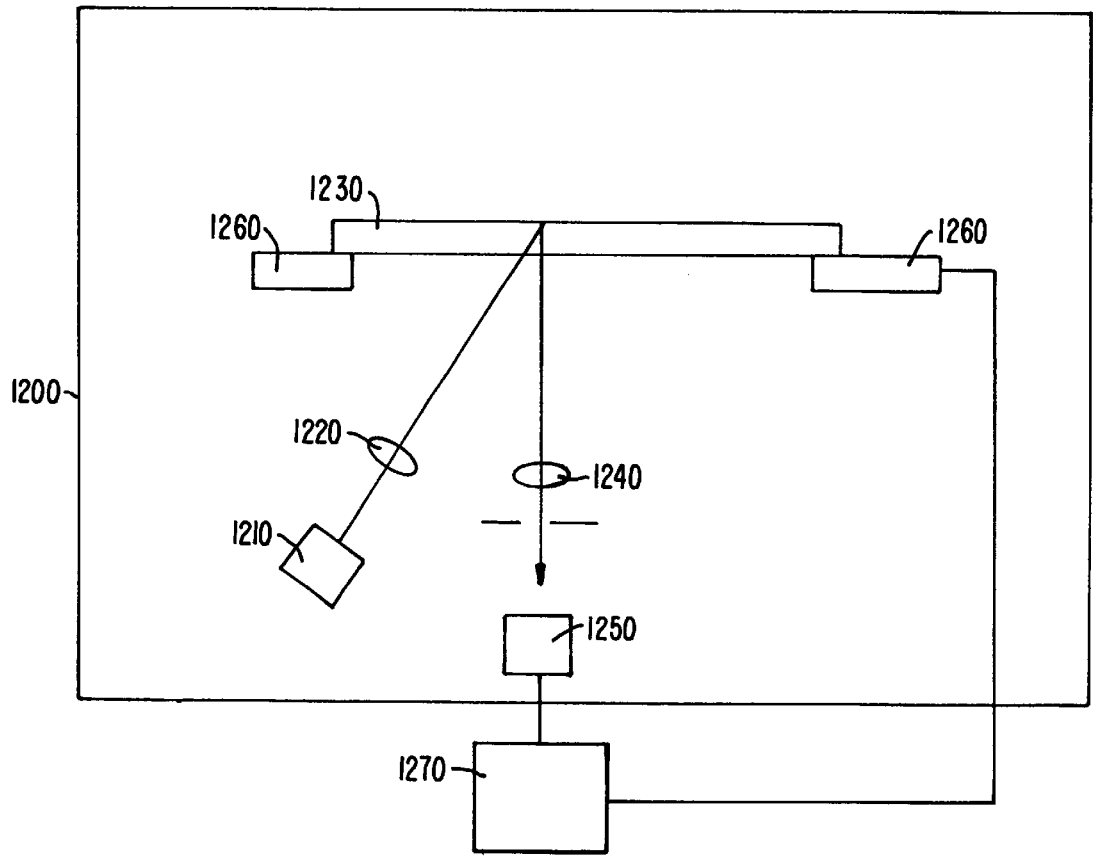
FIG. 12 depicts a chip scanner employing confocal microscope technology.

Referring to FIG. 12, in one embodiment of the invention the chip reader comprises a body 1200 for immobilizing the oligonucleotide array. Excitation radiation, from an excitation source 1210 having a first wavelength, passes through excitation optics 1220 from below the array. The excitation optics cause the excitation radiation to excite a region of an oligonucleotide array on the substrate. In response, labeled material on the sample emits radiation which has a wavelength that is different from the excitation wavelength. Collection optics 1240, also below the array, then collect the emission from the sample and image it onto a detector 1250. The detector generates a signal proportional to the amount of radiation sensed thereon. The signals can be assembled to represent an image associated with the plurality of regions from which the emission originated.

According to one embodiment, a multi-axis translation stage 1260 moves the oligonucleotide array in order to position different areas to be scanned, and to allow different locations of an array to be interrogated. As a result, a 2-dimensional image of the oligonucleotide array is obtained.

The oligonucleotide array reader can include an auto-focusing feature to maintain the sample in the focal plane of the excitation light throughout the scanning process. Further, a temperature controller may be employed to maintain the sample at a specific temperature while it is being scanned. The multi-axis translation stage, temperature controller, auto-focusing feature, and electronics associated with imaging and data collection are managed by an appropriately programmed digital computer 1270.

In one embodiment, a beam is focused onto a spot of about 2 $\mu$m in diameter on-the surface of the array using, for example, the objective lens of a microscope or other optical means to control beam diameter. (See, e.g., U.S. Pat. No. 5,631,734, supra.)

In another embodiment, fluorescent probes are employed in combination with CCD imaging systems. Details of this method are described in U.S. Pat. No. 5,578,832, incorporated herein by reference in its entirely. In many commercially available microplate readers, typically the light source is placed above an array, and a photodiode detector is below the array. For the present methods, the light source can be replaced with a higher power lamp or laser. In one embodiment, the standard absorption geometry is used, but the photodiode detector is replaced with a CCD camera and imaging optics to allow rapid imaging of the array. A series of Raman holographic or notch filters can be used in the optical path to eliminate the excitation light while allowing the emission to pass to the detector. In a variation of this method, a fiber optic imaging bundle is utilized to bring the light to the CCD detector. In another embodiment, the laser is placed below the oligonucleotide array and light directed through the transparent wafer or base that forms the bottom of the oligonucleotide array. In another embodiment, the CCD array is built into the wafer of the oligonucleotide array.

The choice of the CCD array will depend on the number of oligonucleotides in each array. If 2500 ensembles of sequence-specific oligonucleotides nominally arranged in a square (50×50) are examined, and 6 lines in each feature are sampled to obtain a good image, then a CCD array of 300×300 pixels is desirable in this area. However, if an individual array has 48,400 ensembles (220×220) then a CCD array with 1320×1320 pixels is desirable. CCD detectors are commercially available from, e.g., Princeton Instruments, which can meet either of these requirements.

The detection device also can include a line scanner, as described in U.S. Pat. No. 5,578,832, incorporated herein by reference. Excitation optics focuses excitation light to a line at a sample, simultaneously scanning or imaging a strip of the sample. Surface-bound fluorescent labels from the array fluoresce in response to the light. Collection optics image the emission onto a linear array of light detectors. By employing confocal techniques, substantially only emission from the light's focal plane is imaged. Once a strip has been scanned, the data representing the 1-dimensional image are stored in the memory of a computer. According to one embodiment, a multi-axis translation stage moves the device at a constant velocity to continuously integrate and process data. Alternatively, galvometric scanners or rotating polyhedral mirrors may be employed to scan the excitation light across the sample. As a result, a 2-dimensional image of the sample is obtained.

In another embodiment, collection optics direct the emission to a spectrograph which images an emission spectrum onto a 2-dimensional array of light detectors. By using a spectrograph, a full spectrally resolved image of the array is obtained.

The read time for an oligonucleotide array will depend on the photophysics of the fluorophore (i.e., fluorescence quantum yield and photodestruction yield) as well as the sensitivity of the detector. For fluorescein, sufficient signal-to-noise to read a chip image with a CCD detector can be obtained in about 30 seconds using 3 $mW/cm^2$ and 488 nm excitation from an Ar ion laser or lamp. By increasing the laser power, and switching to dyes such as CY3 or CY5 which have lower photodestruction yields and whose emission more closely matches the sensitivity maximum of the CCD detector, one easily is able to read each array in less than 5 seconds.

A computer can transform the data into another format for presentation. Data analysis can include the steps of determining, e.g., fluorescent intensity as a function of substrate position from the data collected, removing "outliers" (data deviating from a predetermined statistical distribution), and calculating the relative binding affinity of the targets from the remaining data. The resulting data can be displayed as an image with color in each region varying according to the light emission or binding affinity between targets and probes therein.

One application of this system when coupled with the CCD imaging system that speeds performance when the detection step involves hybridization of a labeled target oligonucleotide with an oligonucleotide in the array is to obtain results of the assay by examining the on- or off-rates of the hybridization. In one version of this method, the amount of binding at each address is determined at several time points after the targets are contacted with the array. The amount of total hybridization can be determined as a function of the kinetics of binding based on the amount of binding at each time point. Thus, it is not necessary to wait for equilibrium to be reached. The dependence of the hybridization rate for different oligonucleotides on temperature, sample agitation, washing conditions (e.g., pH, solvent characteristics, temperature) can easily be determined in order to maximize the conditions for rate and signal-to-noise. Alternative methods are described in Fodor et al., U.S. Pat. No. 5,324,633, incorporated herein by reference.

The dependence of the hybridization rate for different oligonucleotides on temperature, sample agitation, washing conditions (e.g., pH, solvent characteristics, temperature) can easily be determined in order to maximize the conditions for rate and signal-to-noise.

IX. Mechanics of Assays

Assays on biological arrays generally include contacting an oligonucleotide array with a sample under the selected reaction conditions, optionally washing the array to remove unreacted molecules, and analyzing the biological array for evidence of reaction between target molecules the probes. These steps involve handling fluids. These steps can be automated using automated fluid handling systems for concurrently performing the detection steps on the array. Fluid handling allows uniform treatment of samples in the wells. Microtiter robotic and fluid-handling devices are available commercially, for example, from Tecan AG.

The chip can be manipulated by a fluid-handling device. This robotic device can be programmed to set appropriate reaction conditions, such as temperature, add reagents to the chip, incubate the chip for an appropriate time, remove unreacted material, wash the chip substrate, add reaction substrates as appropriate and perform detection assays. The particulars of the reaction conditions are chosen depends upon the purpose of the assay, for example hybridization of a probe or attachment of a label to oligonucleotides.

If desired, the chip can be appropriately packaged for use in chip reader. One such apparatus is disclosed in U.S. patent application Ser. No. 08/255,682 incorporated herein by reference.

X. Chip Manufacture

In making a chip, the substrate and its surface preferably form a rigid support on which the sample can be formed. The substrate and its surface are also chosen to provide appropriate light-absorbing characteristics. For instance, the substrate may be functionalized glass, Si, Ge, GaAs, GaP, $SiO_2$, $SiN_4$, modified silicon, or any one of a wide variety of gels or polymers such as (poly)tetrafluoroethylene, (poly) vinylidenedifluoride, polystyrene, polycarbonate, or combinations thereof. Other substrate materials will be readily apparent to those skilled in the art upon review of this disclosure. In a preferred embodiment the substrate is flat glass or silica.

Surfaces on the solid substrate usually, though not always, are composed of the same material as the substrate. Thus, the surface may be composed of any of a wide variety of materials, for example, polymers, plastics, resins, polysaccharides, silica or silica-based materials, carbon, metals, inorganic glasses, membranes, or any of the above-listed substrate materials. In one embodiment, the surface will be optically transparent and will have surface Si-OH functionalities, such as those found on silica surfaces.

Preferably, oligonucleotides are arrayed on a chip in addressable rows and columns. Technologies already have been developed to read information from such arrays. The amount of information that can be stored on each chip depends on the lithographic density which is used to synthesize the wafer. For example, if each feature size is about 100 microns on a side, each chip can have about 10,000 probe addresses in a 1 $cm^2$ area.

The following examples are offered by way of illustration, not by way of limitation.

EXAMPLES

A. Coupling Efficiency

Figure 13:
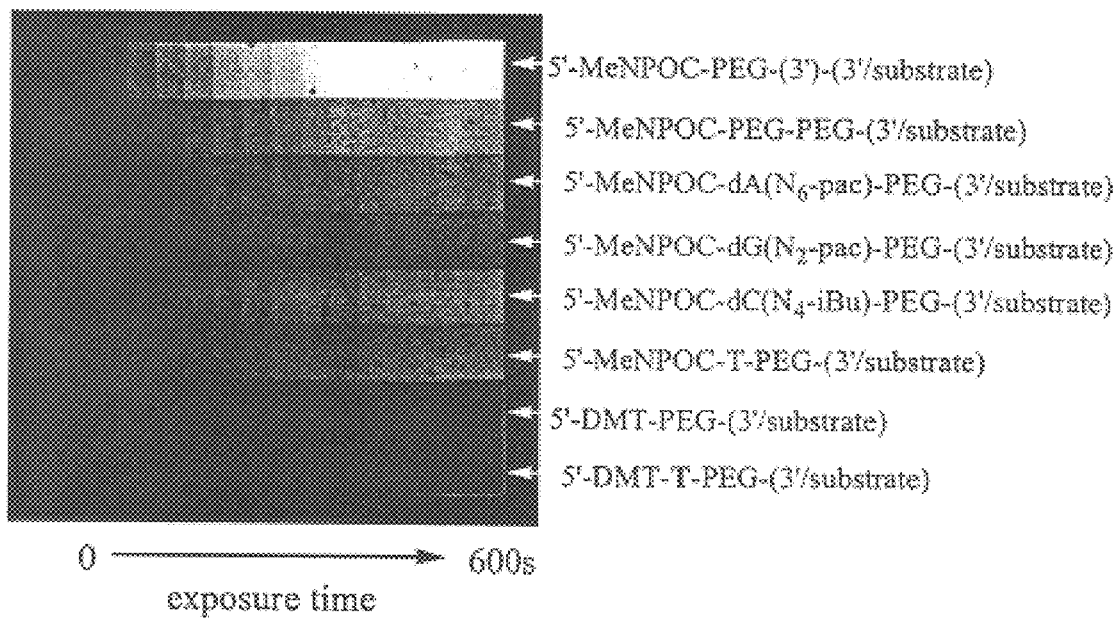
FIG. 13 shows the extent of deprotection caused by exposure of nucleic acids to UV light for varying lengths of time.

This example demonstrates the determination of the efficiency of photo-deprotection of 5'-MeNPOC-monomers. Results are depicted in FIG. 13. Various protected monomers were added to the substrate in horizontal stripes using VLSIPS™ methodology, and then all of the stripes were subjected to progressively increasing exposures to UV light in vertical stripes across the chip (1-r). The extent of deprotection, and hence the surface fluorescence, increased with increasing light exposure, until deprotection was complete and the fluorescence intensity levels off.

B. Depurination

Figure 14:
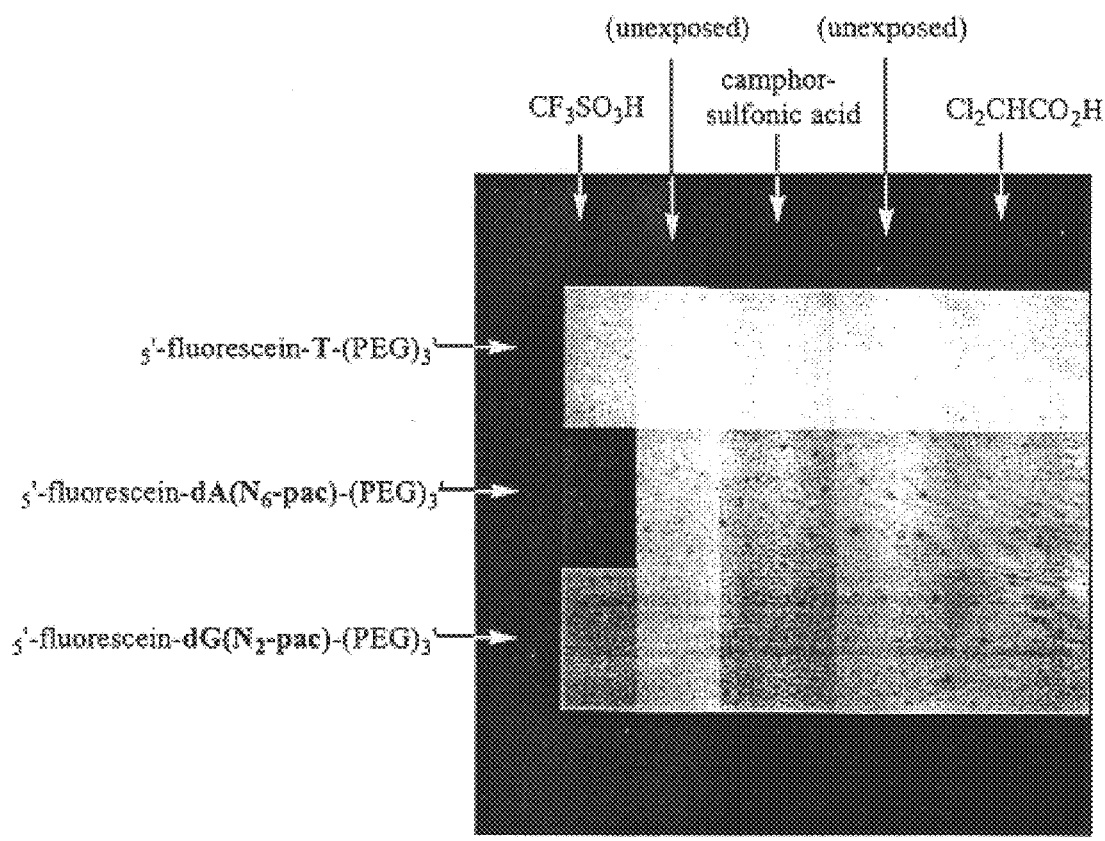
FIG. 14 shows the extent of deprotection caused by exposure of oligo-T, oligo-dA and oligo-dG to triflic acid, camphor-sulfonic acid and dichloroacetic acid.
Figure 15:
FIG. 15 depicts the chemical structure of a useful photoacid generator, di-tertbutyl phenyl iodonium salt.

This example demonstrates the determination of extent of depurination under several conditions. Results are depicted in FIG. 14. Three protected building blocks (DMT-da$^{bz}$, DG$^{ibu}$, & T) were coupled to a surface that had been previously derivatized with the usual bis(hydroxyethl)-aminopropyltriethoxysilane followed by MeNPOC-hexaethylene-glycol-CEP. Each of the monomers was coupled in a separate region (adjacent horizontal stripes) using photolithography. Part of each stripe was then exposed to acids generated in a PAG-polymer film. The PAG used here was a di-tertbutylphenyl iodonium salt dissolved in a polynethylmethacrylate film overlying the substrate, and exposed to 365 nm light to generate the acid HX in the film. The structure of ditertbutyl phenyl iodonium salt is given in FIG. 15. After alkali treatment and fluorescence imaging, it can be seen that in the region of the adenosine-nucleotide stripe exposed to triflic acid, there is a sharp decrease in fluorescence relative to either the non-exposed regions or those exposed to the weaker acids camphorosulfonic and dichloroacetic acid.

The present invention provides a novel method for identifying production parameters in the synthesis of oligonucleotide arrays. While specific examples have been provided, the above description is illustrative and not restrictive. Many variations of the invention will become apparent to those skilled in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

What is claimed is:

1. A quality control process for manufacturing nucleic acid probe arrays comprising manufacturing nucleic acid probe arrays by spatially directed nucleic acid synthesis in high volume and testing arrays selected from among the high volume manufactured.

2. The method of claim 1 wherein the spatially directed nucleic acid synthesis is performed by light-directed nucleic acid synthesis.

3. The method of claim 1 wherein selected arrays are tested for the efficiency of monomer coupling during spatially directed nucleic acid synthesis.

4. The method of claim 1 wherein selected arrays are tested for the amount of deprotection of nucleic acids in the selected arrays.

5. The method of claim 1 wherein selected arrays are tested for the amount of double stranded nucleic acids in the nucleic acid probe array.

6. A testing method comprising:
providing a substrate having a surface with linkers having active sites for nucleic acid synthesis;
synthesizing an ensemble of sequence-specific nucleic acids on the substrate by spatially directed nucleic acid synthesis;
exposing a first area of the substrate to a first test condition;
exposing a second area of the substrate to a second test condition; and
determining the relative amount of nucleic acids having a structural feature in the first and second area, wherein the structural feature is not monomer coupling and the test condition is not exposure to a nucleic acid probe having a sequence complementary to a sequence in the array; whereby the relative amount indicates the relative efficiency to cause the appearance of the structural feature.

7. The method of claim 6 wherein spatially directed nucleic acid synthesis is performed by light-directed nucleic acid synthesis.

8. The method of claim 6 comprising synthesizing at least two ensembles of different sequence-specific nucleic acids on the substrate.

9. The method of claim 6 wherein the nucleic acids have active sites for attaching a detectable label and the step of determining the amount of nucleic acids having the structural feature comprises exposing the nucleic acids to a detectable label under conditions for attachment of the label to nucleic acids having the structural feature, and determining the amount of detectable label attached.

10. The method of claim 9 wherein the detectable label is a fluorescent label, a chemi-luminescent label, a bio-luminescent label, a colorimetric label or a light-scattering label.

11. The method of claim 10 wherein the label is a fluorescein, a rhodamine, a polymethine dye derivative or a phosphor.

12. A method for testing the efficiency of monomer coupling in the synthesis of a nucleic acid probe array by spatially directed nucleic acid synthesis comprising the steps of:
providing a substrate having a surface having linkers with active sites;
coupling first protected monomers to active sites in a first area and at least one second area of the substrate and capping unreacted, unprotected active sites;
deprotecting active sites in the second area(s), coupling second protected monomers to active sites in the second area(s) and capping unreacted, unprotected active sites in the second area(s);
optionally repeating the previous step in at least one subsequent area of the substrate and capping unreacted, unprotected active sites in the subsequent area(s);
determining the amount of competent, uncapped active sites at at least two areas; and
comparing the amounts determined, wherein the comparative amount indicates the efficiency of monomer coupling between the two areas.

13. The method of claim 12 wherein spatially directed nucleic acid synthesis is performed by light-directed nucleic acid synthesis.

14. The method of claim 13 wherein the step of determining the amounts of uncapped active sites comprises the steps of deprotecting active sites in the two areas, exposing deprotected active sites in the two areas to a detectable label for attachment, and determining the amount of detectable label attached in the areas.

15. The method of claim 14 wherein the detectable label is a fluorescent label, a chemi-luminescent label, a bio-luminescent label, a colorimetric label or a light-scattering label.

16. The method of claim 15 wherein the label is a fluorescein, a rhodamine, a polymethine dye derivative or a phosphor.

17. A method for testing the efficiency of monomer coupling in the synthesis of a nucleic acid probe array by spatially directed nucleic acid synthesis comprising the steps of:
providing a substrate having a surface having cleavable linkers wherein the linkers comprise detectable labels releasable upon cleavage of the linkers and active sites for monomer coupling;
coupling at least one monomer to the active sites whereby the detectable labels are coupled to the monomer and capping unreacted, unprotected active sites after at least one coupling step;

cleaving the cleavable linkers to release detectably labelled nucleic acids;

determining the lengths of the released nucleic acids; and comparing the amounts of nucleic acids having a first length and a second length, wherein the comparative amount indicates the efficiency of monomer coupling between the nucleic acids of the first length and the second length.

18. The method of claim 17 wherein spatially directed nucleic acid synthesis is performed by light-directed nucleic acid synthesis.

19. The method of claim 18 wherein the cleavable linker is a sulfone, a disulfide or an ester.

20. The method of claim 18 wherein the lengths are determined by determining the mass of the released nucleic acids by HPLC.

21. The method of claim 18 wherein the detectable label is a fluorescent label, a chemi-luminescent label, a bio-luminescent label, a colorimetric label or a light-scattering label.

22. The method of claim 21 wherein the label is a fluorescein, a rhodamine, a polymethine dye derivative or a phosphor.

23. A method for comparing the relative efficiency of two test conditions to cause deprotection of nucleic acids synthesized on a substrate by spatially directed nucleic acid synthesis comprising the steps of:

providing a substrate on which an ensemble of sequence-specific nucleic acids has been synthesized, wherein the active sites on the free terminal nucleotides of the nucleic acids bear a protecting group;

exposing a first area of the substrate to a first test condition;

exposing a second area of the substrate to a second test condition; and determining the amount of unprotected active sites in the first and second areas, whereby the relative amount indicates the relative efficiency.

24. The method of claim 23 wherein spatially directed nucleic acid synthesis is performed by light-directed nucleic acid synthesis.

25. The method of claim 24 wherein the step of determining the amount of unprotected active sites comprises the step of exposing the nucleic acids in the area to a detectable label for attachment to unprotected active sites, and determining the amount of detectable label attached in the area.

26. The method of claim 25 wherein the detectable label is a fluorescent label, a chemi-luminescent label, a bio-luminescent label, a colorimetric label or a light-scattering label.

27. The method of claim 26 wherein the label is a fluorescein, a rhodamine, a polymethine dye derivative or a phosphor.

28. The method of claim 23 wherein a substrate is provided on which at least two ensembles of different sequence-specific nucleic acids have been synthesized by spatially directed nucleic acid synthesis, and at least two areas of the substrate, each area having a different sequence-specific nucleic acid, are exposed to the same test condition.

29. The method of claim 24 wherein the test condition is exposure to light, acid, base, nucleophilic agent, reducing agent or oxidizing agent.

30. A method of determining whether an ensemble of nucleic acids synthesized on a substrate by spatially directed nucleic acid synthesis contains double-stranded nucleic acids formed from the nucleic acids within themselves or between nucleic acids in the ensemble comprising:

providing a substrate on which an ensemble of sequence-specific nucleic acids has been synthesized in an area of the substrate, wherein nucleic acids in the ensemble are attached to a detectable label that is released from the area upon cleavage of the nucleic acids;

contacting the ensemble with an agent that cleaves double-stranded nucleic acids, whereby cleavage of nucleic acids formed into double stranded nucleic acids releases detectable label from the area; and determining the amount of detectable label remaining the area, whereby the amount of detectable label is inversely related to the amount of double-stranded nucleic acids.

31. The method of claim 30 wherein spatially directed nucleic acid synthesis is performed by light-directed nucleic acid synthesis.

32. The method of claim 31 wherein the detectable label is a fluorescent label, a chemi-luminescent label, a bio-luminescent label, a colorimetric label or a light-scattering label.

33. The method of claim 32 wherein the label is a fluorescein, a rhodamine, a polymethine dye derivative or a phosphor.

34. The method of claim 31 comprising synthesizing at least two ensembles of different a sequence-specific nucleic acids on the substrate.

35. The method of claim 31 wherein the cleavage agent is an endonuclease.

36. The method of claim 35 wherein the endonuclease is a restriction endonuclease.

37. The method of claim 1 wherein high volume is the manufacture of at least 10 nucleic acid probe arrays per day from a single fabrication machine or in a single fabrication facility.

38. The method of claim 1 wherein high volume is the manufacture of at least 50 nucleic acid probe arrays per day from a single fabrication machine or in a single fabrication facility.

39. The method of claim 1 wherein high volume is the manufacture of at least 500 nucleic acid probe arrays per day from a single fabrication machine or in a single fabrication facility.

* * * * *